United States Patent [19]

Palumbo et al.

[11] Patent Number: 5,055,269
[45] Date of Patent: Oct. 8, 1991

[54] TEMPERATURE LIMITED CATALYTIC GAS DETECTOR APPARATUS

[75] Inventors: Perry A. Palumbo, New Kensington; Oscar Singleton, Pittsburgh; Louis G. Gaetano, New Kensington, all of Pa.

[73] Assignee: Bacharach, Inc, Pittsburgh, Pa.

[21] Appl. No.: 319,745

[22] Filed: Mar. 6, 1989

[51] Int. Cl.$^5$ ............................................. G01N 27/16
[52] U.S. Cl. .................................... 422/96; 422/94; 340/633; 73/23.31; 324/706
[58] Field of Search ......................... 422/94, 95, 96; 73/23.31; 324/443, 706; 340/633, 634

[56] References Cited

U.S. PATENT DOCUMENTS

| | | | |
|---|---|---|---|
| 3,577,074 | 5/1971 | Praglin | 324/98 |
| 3,678,489 | 7/1972 | Scherban et al. | 340/237 |
| 3,908,164 | 9/1975 | Parker | 323/75 |
| 4,112,356 | 9/1978 | Toy | 324/71 |
| 4,202,666 | 5/1980 | Hall et al. | 23/232 |
| 4,263,588 | 4/1981 | Gautier | 340/632 |
| 4,305,724 | 12/1981 | Micko | 23/232 |
| 4,317,796 | 3/1982 | Barr | 422/95 |
| 4,332,772 | 6/1982 | McNally | 422/97 |
| 4,444,056 | 4/1984 | Romo | 73/708 |
| 4,476,096 | 10/1984 | Hoht | 422/96 |
| 4,533,520 | 8/1985 | Bossart et al. | 422/96 |
| 4,541,988 | 10/1985 | Tozier et al. | 422/94 |
| 4,758,837 | 7/1988 | Fruhwald | 340/870 |

OTHER PUBLICATIONS

Delphian Technical Note No. 24.

Primary Examiner—David L. Lacey
Assistant Examiner—David Redding
Attorney, Agent, or Firm—Webb, Burden, Ziesenheim & Webb

[57] ABSTRACT

A temperature limited catalytic gas detector includes a catalytic gas sensor in one branch of a Wheatstone bridge network. A power supply is connected through a voltage controlled regulator to the bridge network. An instrumentation amplifier measures electrical imbalances across the bridge network. A display is connected to the output of the instrumentation amplifier. The detector also includes a comparator which compares the output of the instrumentation amplifier with a predetermined limit signal and produces an output when the output of the instrumentation amplifier exceeds the limit voyage. The regulator is responsive to the output of the comparator to thereby reduce the power supply to the bridge network. The limit signal is equivalent to the output of the instrumentation amplifier when the gas sensor is at a particular high temperature. The arrangement prevents the gas sensor from operating at excessive operation temperatures.

20 Claims, 3 Drawing Sheets

TEMPERATURE LIMITED CATALYTIC GAS DETECTOR APPARATUS

1. FIELD OF THE INVENTION

This invention relates to combustible gas detectors and, more particularly, to the automatic protection of catalytic gas sensors from damaging, high operating temperatures.

2. DESCRIPTION OF THE PRIOR ART

The use of catalytic sensors to measure the concentration of combustible gases is well known. In general, the sensor is a resistive element coated with a catalytic material which will react with a particular gas. A current is passed through the resistive element at an amperage sufficient to heat the catalytic coating to a desired operating temperature. As the gas passes over the sensor and contacts the catalytic coating, it will chemically react therewith in an exothermic reaction and add heat to the sensor, thus heating the resistive element therein. This temperature increase will proportionally raise the resistance of the sensor. Thus, the increase in resistance of the sensor is directly related to the concentration of the gas contacting the sensor.

This change of sensor resistance can be detected electrically in any number of ways to provide a direct reading of the gas concentration. In a common arrangement, a catalytic sensor, combining an active element in series with a reference element, is provided in one branch of a Wheatstone bridge. A pair of fixed resistors in series with each other forms the other branch of the Wheatstone bridge. A voltage difference is applied across the branches of the bridge and the voltages at the points between the fixed resistors and between the active and reference elements are monitored. The relationship of the fixed resistors is either selected initially or adjusted in known manners so that the voltages at these points are equal, i.e., the bridge is balanced, before any gas contacts the sensor.

In one known catalytic sensor, the active and reference elements are each formed from a coiled platinum or platinum/iridium alloy wire coated with an insulating ceramic material, such as alumina or glass. The active element alone is then coated with a catalytic material, such as platinum black. The gas undergoing detection will react with the catalytic coating on the active element and change its resistance as described above, thus causing an imbalance in the Wheatstone bridge circuit. This imbalance is detected as a voltage difference across the point between the fixed resistors and the point between the active and reference elements. This voltage difference is usually measured by an instrumentation amplifier or the like and displayed on a voltmeter or other common indication means. The measured voltage difference is directly related to the concentration of the gas contacting the sensor. Usually the gas is caused to contact both the reference and active elements so that any resistance changes in the sensor resulting from the gas contact, other than those from the catalytic material on the active element, are balanced and add no additional voltage imbalance in the bridge circuit. However, it is not necessary for the gas to contact the reference element of the sensor. Typical Wheatstone bridge arrangements are shown, for example, in U.S. Pat. Nos. 4,332,772 and 3,577,074 and in Delphian Technical Note No. 24.

An ongoing problem with the use of any catalytic combustible gas sensor is overheating. The catalytic element must be heated initially to upwards of 500° C. before it will react with the gas. Moreover, the sensor will be heated further while the gas and catalytic material are undergoing the exothermic chemical reaction. Excessive heat will both shorten the life of the sensor and effect its subsequent operation. For example, if the sensor becomes too hot, the heating element is partially boiled away, creating a hot, thin section Such a section creates a gradual drifting, up or down, at an increasing rate until the element opens and fails totally. This problem is a particular concern when a sensor is used after being exposed to a gas in concentrations greater than 100% of its lower explosive limit or at the stoichiometric point for the gas. Overheating also renders the catalyst less active, such as by sintering the platinum black particles. As a result, the magnitude of the sensor output decreases and amplification of the output must be increased to maintain a consistent reading over time.

Various prior art arrangements have been developed to protect a catalytic gas sensor from the overheating problems discussed above. Maintaining the sensor temperature constant while operating over a wide range of conditions has been carried out. See U.S. Pat. Nos. 4,541,988; 4,533,520; 4,317,796; 4,305,724 and Delphian Technical Note No. 24. The problem with these arrangements is that they are complicated and expensive. The system disclosed in U.S. Pat. No. 3,678,489 totally disconnects the sensor from the power source when the gas concentration reaches a certain level. However, removing totally the current from the sensor negatively effects subsequent operation of the sensor since it has an inherent recovery time. A variety of other complicated arrangements for protecting catalytic and other sensors from temperature effects have been developed. U.S. Pat. Nos. 4,476,096; 4,444,056; 4,263,588; 4,202,666; 4,112,356; and 3,908,164.

It is an object of the present invention to provide an arrangement for automatically protecting a catalytic or other gas sensor from excessive and damaging temperatures. It is a further object to provide for such an arrangement in a simple, economical and easy to manufacture manner. It is yet another object to minimize the recovery time between normal and protected operation and to avoid the deleterious effects of totally removing the power from such a sensor for any period of time.

SUMMARY OF THE INVENTION

Accordingly, we have invented a temperature limited gas detector arrangement, particularly suitable for use with catalytic gas sensors, which includes a gas sensor positioned within a detection circuit, such as a Wheatstone bridge network. A power supply is connected through a control means, such as a voltage controlled regulator, to the detection circuit. The apparatus also includes means for measuring electrical signals generated by the detection circuit as a particular gas contacts the gas sensor. In a Wheatstone bridge network, the measuring means could be an instrumentation amplifier measuring imbalances developed across the bridge. A display means, such as a meter or the like, is connected to an output of the measuring means.

The apparatus also includes a comparison means, such as an on/off comparator, for comparing the output of the measuring means with a predetermined limit signal and producing an output signal when the output of the measuring means exceeds the limit signal. The control means is responsive to the output of the comparison means to thereby reduce the power supplied to the detection circuit. The limit signal is equivalent to the output of the measuring means when the gas sensor is at a particular temperature.

This invention is particularly useful for a catalytic gas sensor including an active element in series with a reference element and positioned in one branch of a Wheatstone bridge network. The detector can also be incorporated in a circuit including a 4-20 milliampere transmitter which receives the output of the measuring means and the output of the detection circuit. The limit signal can be produced either by a band gap reference, a resistive network connected to a fixed voltage source, or any other known means for producing a predetermined fixed electrical signal. The arrangement can further include an alarm means for indicating when the temperature of the gas sensor exceeds the particular temperature. The alarm means can be a light emitting diode or other known alarms.

DETAILED DESCRIPTION OF THE PREFERRED EMBODIMENTS

Figure 1:
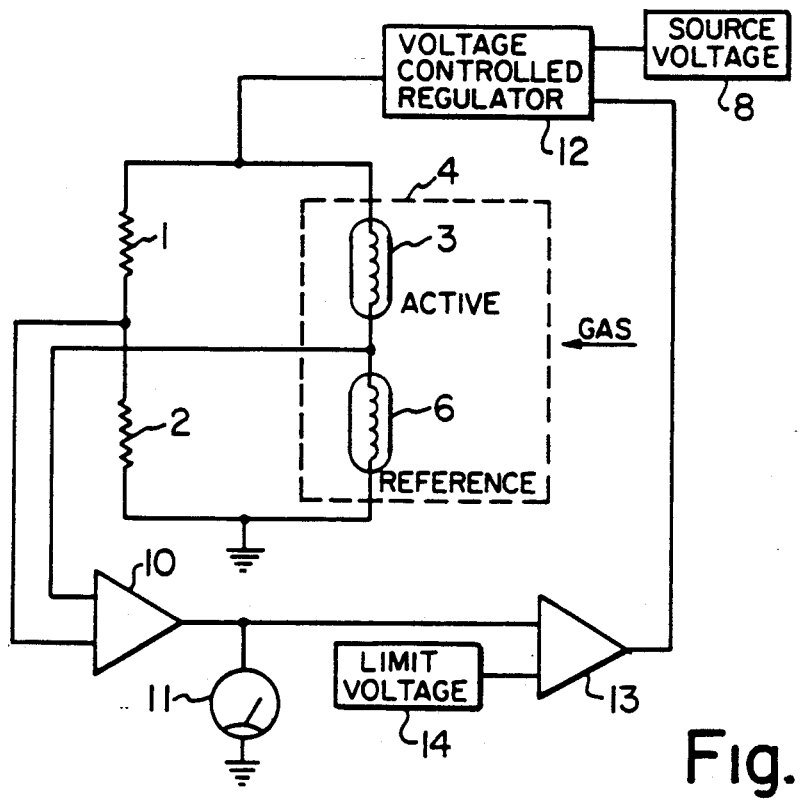
FIG. 1 is a schematic diagram showing the basic elements of a temperature limited catalytic gas detector in accordance with the present invention.

A Wheatstone bridge, catalytic gas detector arrangement including the temperature limiting protection feature of the present invention is shown in FIG. 1. The Wheatstone bridge is formed of resistor 1 and resistor 2 in series in one branch of the bridge and the gas sensor 4, formed of an active element 3 and a reference element 6 in series, in the other branch of the bridge. The branches of the bridge are joined together at resistor 1 and the active element 3 and connected to a source voltage 8. The branches of the bridge are joined together at resistor 2 and the reference element 6 and are either grounded, as shown, or connected to another terminal on the source voltage 8. The voltage developed at a point between resistor 1 and resistor 2, i.e., across resistor 2, is supplied to one input of an instrumentation amplifier 10. The voltage developed at a point between the active element 3 and the reference element 6, i.e., across the reference element 6, is supplied to the other input of the instrumentation amplifier 10. The output of the instrumentation amplifier 10 is supplied to a meter 11 or the like.

The arrangement described above is a standard Wheatstone bridge, catalytic gas detector arrangement. Resistors 1 and 2 of the bridge are selected or adjusted so that the bridge is balanced when no gas is contacting the gas sensor 4. As a result, no voltage difference is detected by the instrumentation amplifier 10 and no signal is developed at the meter 11. The source voltage 8 causes current to flow through the gas sensor 4 and heat the active element 3 to a sufficient temperature to enable the catalytic material thereon to react with the gas being detected. As the gas flows over the gas sensor 4 and reacts with the catalytic material on the active element 3, the resistance of the active element 5 changes and the Wheatstone bridge becomes imbalanced. The magnitude of the imbalance is indicated by the meter 11 and is a direct reading of the concentration of the gas contacting the gas sensor 4.

In accordance with the present invention, the source voltage 8 is passed through a voltage controlled regulator 12 before being supplied to the Wheatstone bridge. The output of the instrumentation amplifier 10 is also supplied to one input of a comparator 13 and a fixed limit voltage 14 is supplied to the other input of the comparator 13. The output of the comparator 13 is supplied to the voltage controlled regulator 12 and controls the magnitude of the voltage supplied to the Wheatstone bridge. The limit voltage 14 is selected to be greater than the output of the instrumentation amplifier 10 under normal operation, at lower temperatures and lower gas concentrations.

As long as the output of the instrumentation amplifier 10 remains smaller than the limit voltage 14, the comparator 13 produces no output and does not change the output voltage of the voltage controlled regulator 12. Under these conditions, a constant voltage is supplied to the Wheatstone bridge, the gas sensor 4 detects concentrations of gas in a normal manner, and the circuit develops meaningful signals at the meter 11.

If the output of the instrumentation amplifier 10 exceeds the limit voltage 14, the comparator 13 will then produce an output which will cause the voltage controlled regulator 12 to supply a lower voltage to the Wheatstone bridge. In a preferred embodiment, the comparator 13 produces the same output regardless of the amount by which the output of the instrumentation amplifier 10 exceeds the preset limit voltage 14. As a result, a constant, lower voltage will be supplied to the bridge network after the instrumentation amplifier 10 output exceeds the limit voltage 14. It is also possible to continually reduce the output of the voltage controlled regulator 12 as the output of the instrumentation amplifier 10 grows continually larger than the limit voltage 14.

By selecting the limit voltage 14 to be equal to the output of the instrumentation amplifier 10 when the gas concentrations at the gas sensor 4 reach a critical level, such as at 100% of the lower explosive limit of the gas or when the meter 11 is reading full scale, the circuit will protect the gas sensor 4 from overheating. When the limit voltage 14 is exceeded, the voltage supplied to the bridge will be reduced and will limit the actual temperature on the active element 3 and reference element 6. Even though the gas concentrations contacting the gas sensor 4 may increase, and will normally tend to cause the gas sensor 4 to increase in temperature, the increase in temperature from catalytic activity will be more than offset by the reduction in voltage supplied to the bridge. At this point, normal measuring operation of the sensor 4 cannot continue since the initial, fixed voltage supplied to the bridge has been changed. However, this is not important since the meter 11 is already at full scale reading and will provide no greater output with further increases in gas concentration.

By automatically limiting the voltage supplied to the bridge network as the output signal developed thereby exceeds a critical level, the gas sensor 4 will not be subjected to damaging overheating conditions. Moreover, the recovery time for a return to normal operation is kept at a minimum since power has been supplied to the gas sensor 4 during the entire operation.

Figure 2:
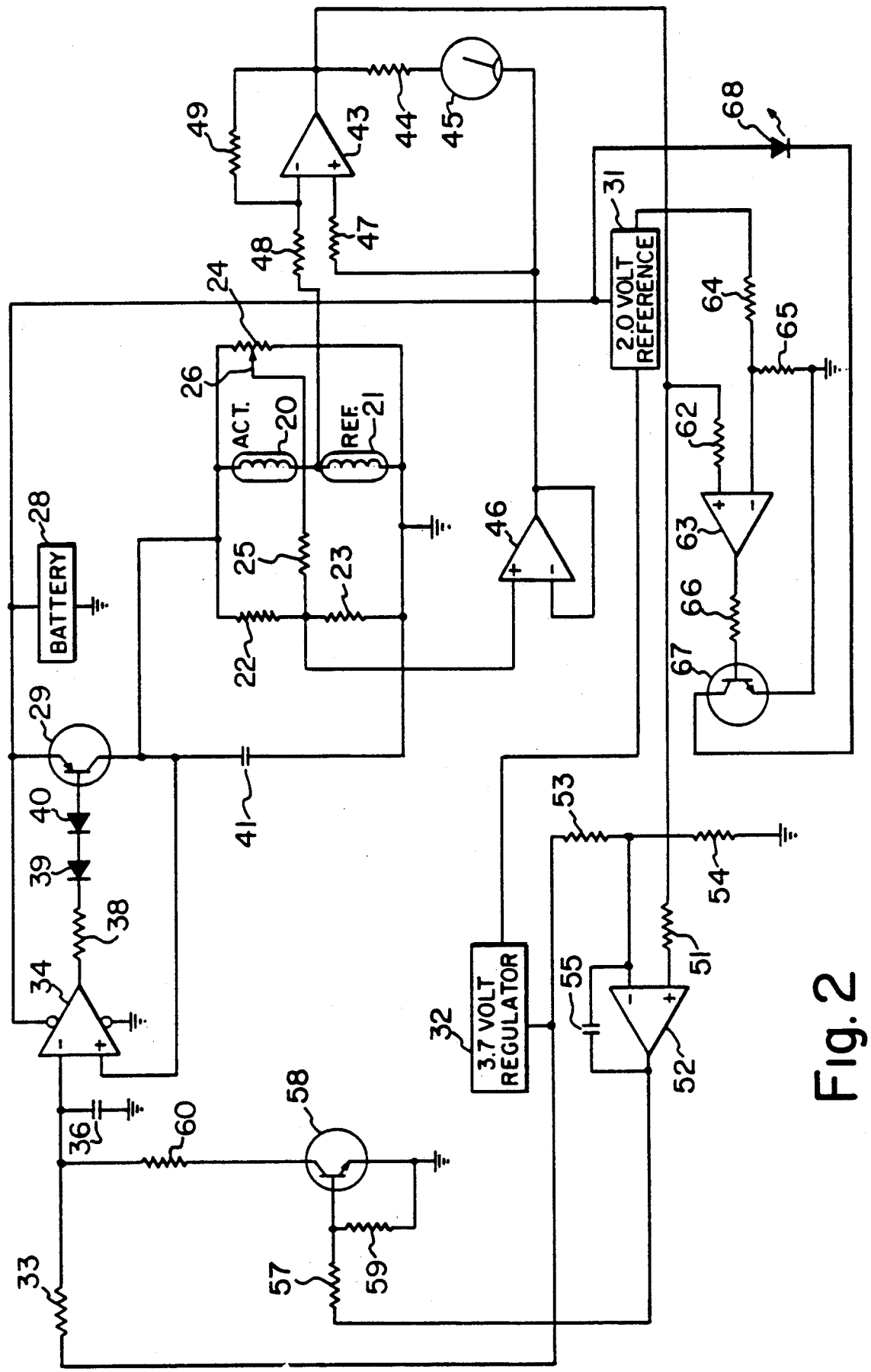
FIG. 2 is a circuit diagram showing one embodiment of a gas detector system incorporating the temperature limiting arrangement of the present invention.

A circuit for a portable, battery operated gas detector, including the improvement of the present invention is shown in FIG. 2. A Wheatstone bridge network is formed with a gas sensor, including an active element 20 in series with a reference element 21, in one branch and series resistors 22 and 23 in the other branch. A potentiometer 24 extends parallel to the bridge to provide for zero adjustment, and a resistor 25 extends from the movable contact 26 of potentiometer 24 to a point between resistors 22 and 23 and sets the sensitivity of the zero adjustment. The branches of the bridge network are grounded at resistor 23 and the reference element 21 and a voltage from battery 28 is supplied through pnp transistor 29 to the branches of the bridge network at resistor 22 and the active element 20.

The battery 28, which is on the order of 5-6 volts, is also connected to a standard 2.0 volt reference 31, which has an output connected to a standard 3.7 volt regulator 32, which produces a steady 3.7 volt output. The output of regulator 32 is supplied through resistor 33 to the negative input of operational amplifier 34. Noise filtering capacitor 36 extends between ground and the negative input of amplifier 34. Extending in series between the output of amplifier 34 and the base of pnp transistor 29 are resistor 38, connected to the cathode of diode 39 which has its anode connected to the cathode of diode 40. Resistor 38 and diodes 39 and 40 provide a biasing signal to the base of transistor 29. The battery 28 is connected to both amplifier 34 and to the emitter of transistor 29. The collector of transistor 29 is connected to the bridge network at resistor 22 and the active element 20, to the positive input of amplifier 34, and to ground through noise filtering capacitor 41. Regulator 32, resistors 33 and 38, capacitors 36 and 41, diodes 39 and 40, and transistor 29 together form a voltage controlled regulator which supplies a fixed voltage, here 3.7 volts, to the bridge network regardless of variations or fluctuations in the voltage of the battery 28.

Imbalances in the bridge are measured by operational amplifier 43 having an output connected through resistor 44 to meter 45. The bridge voltage across resistor 23 is supplied to the positive input of buffer amplifier 46 and the output of amplifier 46 is supplied through impedance matching resistor 47 to the positive input of amplifier 43. The output of amplifier 46 is fed back to its negative input. The arrangement of the buffer amplifier 46 is provided for improved impedance matching, but is not necessary for the operation of the circuit. The bridge voltage across the reference element 21 is supplied through impedance matching resistor 48 to the negative input of amplifier 43. Feedback resistor 49 extends between the output and the negative input of amplifier 43. Resistors 48 and 49 determine the gain ratio of amplifier 43 in a known manner.

The output of amplifier 43 is supplied through impedance matching resistor 51 to the positive input of comparator 52. The 3.7 volt output of regulator 32 is supplied to series resistors 53 and 54, which are connected to ground. The voltage across resistor 54 is supplied to the negative input of comparator 52. By appropriately selecting the values for resistors 53 and 54, the 3.7 volt output of regulator 32 is reduced to any desired value and supplied to the comparator for comparison purposes with the output from amplifier 43. The comparator 52 has an on/off voltage output, remaining at zero when the voltage at its positive input remains lower than the voltage at its negative input, and raising to full scale output when the voltage at its positive input exceeds the voltage at its negative input. Since the voltage at the negative input of comparator 52 remains fixed as determined by regulator 32 and resistors 53 and 54, and can be referred to as the limit voltage, the comparator 52 will have a voltage output only when the voltage generated by bridge imbalances through amplifier 43 exceeds the predetermined limit voltage. Capacitor 55 extending between the output and the negative input of comparator 52 functions as an integrator to slow down the response of the comparator 52 and avoid unwanted oscillations.

The output of comparator 52 is supplied through resistor 57 to the base of npn transistor 58. The base of transistor 58 is connected through resistor 59 to ground and the emitter of transistor 58 is connected directly to ground. The collector of transistor 58 is connected through resistor 60 to the negative input of amplifier 34. Resistors 57, 59 and 60 and transistor 58, which are controlled by the output of comparator 52, control the operation of the voltage regulator formed by resistors 33 and 38, capacitors 36 and 41, amplifier 34, diodes 39 and 40, and transistor 29. When the comparator 52 has no output, transistor 58 is in a non-conductive state and the voltage regulator produces a 3.7 volt output supplied to the bridge network as described above. When the comparator 52 produces an output, a voltage is supplied to the base of transistor 58, thus rendering it conductive and opening a current path through resistor 60 to ground. The 3.7 volt voltage supplied to the negative input of amplifier 34 will be reduced by the ratio of the resistance of resistor 60 and the sum of the resistances of resistor 33 plus resistor 60, minus the voltage drop across transistor 58. As a result, the voltage output of the regulator, which is supplied to the bridge network, will be reduced to a lower value, but will not shut off completely. In this arrangement, the voltage supplied to the bridge network will be about 1.4 volts when the comparator 52 produces an output voltage. By selecting the size of the components appropriately, particularly resistors 53 and 54, the comparator 52 will produce an output voltage when the gas sensor is subject to excessively high temperatures.

The circuit shown in FIG. 2 has an optional alarm for indicating when a high temperature condition exists at the gas sensor. The output of amplifier 43 is supplied through resistor 62 to the positive input of operational amplifier 63. The 2.0 volt reference 31 is reduced by series resistors 64 and 65 and supplied to the negative input of amplifier 63. The output of amplifier 63 is supplied through resistor 66 to the base of npn transistor 67. A light emitting diode 68 is connected between the battery 28 and the collector of transistor 67, with the emitter of transistor 67 connected directly to ground. Amplifier 63 functions as a comparator and produces no output as long as the signal supplied to the negative input remains lower than that supplied to the positive input. When amplifier 63 produces no output voltage, transistor 67 remains off and current cannot flow through the light emitting diode 68, which remains dark. By selecting resistors 64 and 65 appropriately, amplifier 63 will produce an output voltage when the gas sensor is subject to excessive temperatures. Transistor 67 will be rendered conductive and current will flow from the battery 28, through the light emitting diode 68, through transistor 67, and to ground. The light emitting diode 68 will light and give a visual alarm that the gas sensor has reached an excessive operating temperature. Other types of alarms, such as an audio alarm, can be used in addition to or in replacement of the light emitting diode 68.

Figure 3:
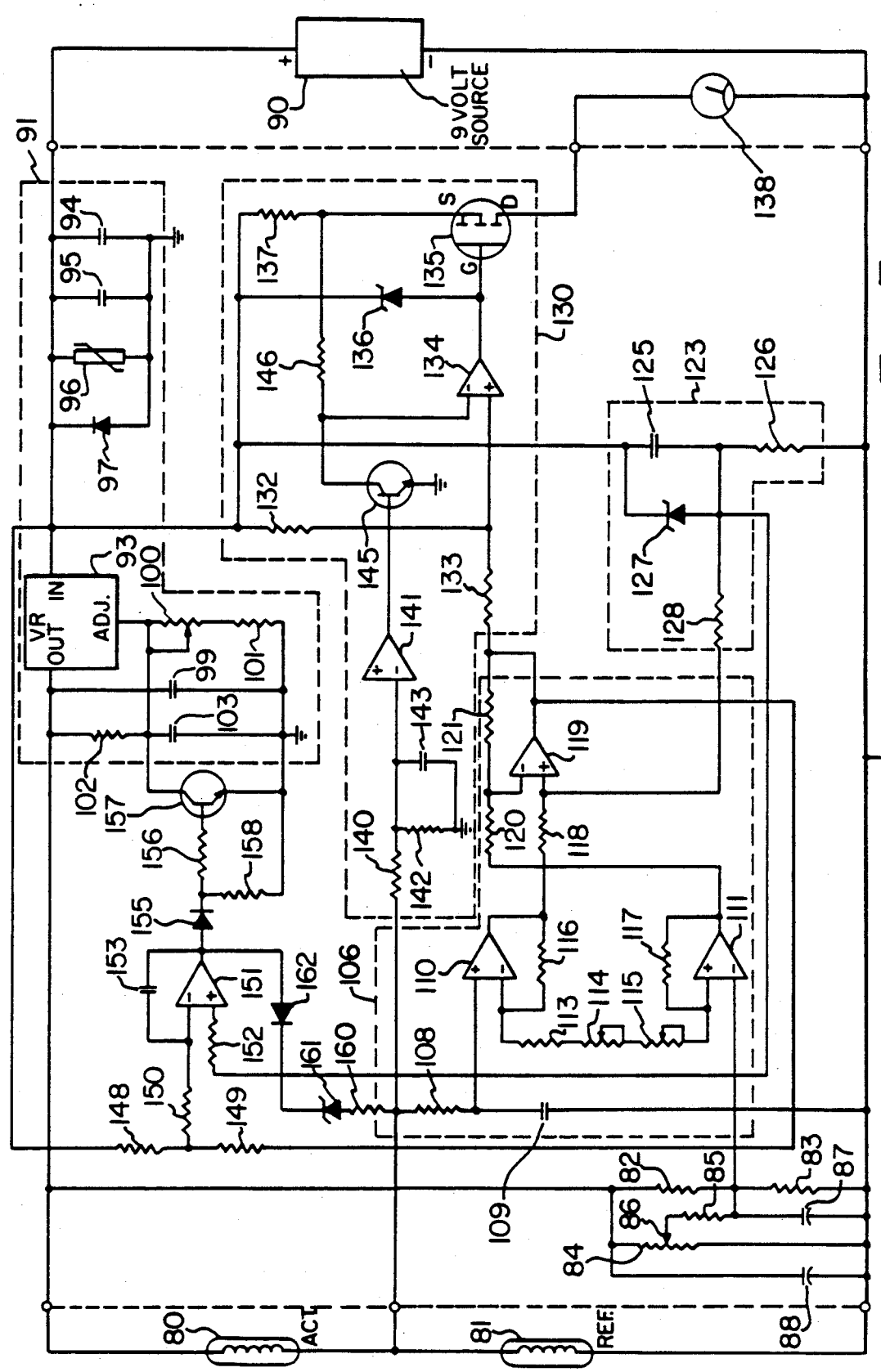
FIG. 3 is a circuit diagram showing another embodiment of a gas detection system incorporating the temperature limiting arrangement of the present invention.

A gas sensor arrangement incorporating a 4-20 milliampere transmitter, including the improvements of the present invention, is shown in detail in FIG. 3. A Wheatstone bridge network is formed with a gas sensor including an active element 80 in series with a reference element 81 in one branch and series resistors 82 and 83 in the other branch. Potentiometer 84 extends parallel to the bridge to provide for zero adjustment, and resistor 85 extends from the movable contact 86 of potentiometer 84 to a point between resistors 82 and 83 and sets the sensitivity of the zero adjustment. A noise filtering capacitor 87 extends in parallel with resistor 83 and noise filtering capacitor 88 extends parallel to the bridge. The branches of the bridge network are grounded at resistor 83 and the reference element 81 and a nine volt battery 90 is supplied through a voltage controlled regulator network 91 to the branches of the bridge network at resistor 82 and the active element 80.

The voltage controlled regulator network 91 includes a standard voltage regulator 93 which has its input connected directly to the nine volt source 90 and has its output connected directly to the bridge network. Extending in parallel from the input of the voltage regulator 93 and ground are capacitors 94 and 95, metal oxide varistor 96 and diode 97. Capacitors 94 and 95 filter out noise in the signal supplied to the voltage regulator 93 and diode 97 bleeds the charge from these capacitors. The metal oxide varistor 96 keeps the voltage supplied to the voltage regulator 93 from exceeding a maximum level and, as a result, protects the gas sensor from excessive, damaging voltages. The output of the voltage regulator 93 is connected through filtering capacitor 99 to ground. A rheostat 100 and resistor 101 extend in series between the adjustment terminal of the voltage regulator 93 and ground. The output of the voltage regulator 93 is also connected through series resistor 102 and filtering capacitor 103 to ground. The adjustment terminal of the voltage regulator 93 is also connected directly to the point between resistor 102 and capacitor 103. The combination of rheostat 100 and resistors 101 and 102 determine the output voltage which is generated by the voltage regulator 93. Resistors 101 and 102 are sized and the rheostat 100 is fine tuned to produce the desired voltage output from regulator 93 which is supplied to the bridge network.

Imbalances in the bridge network are measured by an instrumentation amplifier 106. The bridge voltage across the reference element 81 is supplied through resistor 108 in series with capacitor 109 which is connected to ground. The voltage developed across capacitor 109 is supplied to the positive input of amplifier 110. The voltage across resistor 83 in the bridge network is supplied to the negative input of amplifier 111. Extending in series between the negative input of amplifier 110 and the positive input of amplifier 111 are, in turn, resistor 113, rheostat 114 and rheostat 115. The output of amplifier 110 is fed back through resistor 116 to its negative input and the output of amplifier 111 is fed back to its positive input through resistor 117. The output of amplifier 110 is supplied through resistor 118 to the positive input of amplifier 119 and the output of amplifier 111 is supplied through resistor 120 to the negative input of amplifier 119. Feedback resistor 121 extends between the output of amplifier 119 and its negative input.

The output of a biasing circuit 123 is connected to the positive input of amplifier 119 of the instrumentation amplifier 106. The biasing circuit 123 includes capacitor 125 in series with resistor 126, with capacitor 125 connected to the nine volt source 90 and resistor 126 connected to ground. A band gap reference 127 extends in parallel across capacitor 125. Resistor 128 extends between the jointure of capacitor 125 and resistor 126 to the positive input of amplifier 119. Biasing circuit 123 provides additional voltage to the instrumentation amplifier 106.

The output of the instrumentation amplifier 106 is supplied to a 4-20 milliampere transmitter 130. In addition, the voltage developed across the reference element 81 is supplied to the 4-20 milliampere transmitter 130. Resistors 132 and 133 extend in series, respectively, between the nine volt source 90 and the output of the instrumentation amplifier 106. The voltage at a point between resistors 132 and 133 is supplied to the positive input of amplifier 134. The output of amplifier 134 is supplied to the gate of output transistor 135, which is preferably a p channel enhancement field effect transistor. A band gap reference 136 is connected between the output of amplifier 134 and the nine volt source 90. Resistor 137 extends between the source of output transistor 135 and the nine volt source 90. The drain of output transistor 135 is connected to a meter 138 which in turn is connected to ground.

The voltage across reference element 81 is connected through resistor 140 to the negative input of amplifier 141, which has a internal 0.2 volt reference supplied to its positive input. Parallel RC network of resistor 142 and capacitor 143 extend between the negative input of amplifier 141 and ground. The output of amplifier 141 is connected to the base of npn transistor 145 which has its emitter grounded. The collector of transistor 145 is connected to the negative input of amplifier 134. The collector of transistor 145 is also connected through resistor 146 to the source of output transistor 135. The details of the 4-20 milliampere transmitter do not per se form a part of this application and are described in more detail in U.S. Pat. No. 4,758,837 assigned to the assignee of the present application. The disclosure of U.S. Pat. No. 4,758,837 is incorporated herein by reference.

In accordance with the present invention, resistors 148 and 149 are connected in series between the nine volt source 90 and the output of amplifier 119 in the instrumentation amplifier 106. The voltage at the point between resistors 148 and 149 is supplied through impedance matching resistor 150 to the negative input of operational amplifier 151. The fixed voltage developed at the anode of band gap reference 127 in the biasing circuit 123 is supplied through impedance matching resistor 152 to the positive input of amplifier 151. Feedback capacitor 153 extends between the output of amplifier 151 and its negative input. The output of amplifier 151 is connected through series diode 155 and resistor 156 to the base of npn transistor 157. Resistor 158 extends from the cathode of diode 155 to ground. The emitter of transistor 157 is connected directly to ground and the collector of transistor 157 is connected to a point between resistor 102 and capacitor 103, which in turn is connected to the adjustment input of voltage regulator 93.

Amplifier 151 functions as a comparator to compare the output voltage of the instrumentation amplifier 106 with a preset voltage indicative of an excess temperature condition. By selecting resistors 148 and 149 appropriately, amplifier 151 will produce an output voltage only when the gas sensor is functioning in an excess temperature condition. At this point, amplifier 151 renders transistor 157 conductive and reduces the voltage supplied to the adjustment terminal of the voltage regulator 93 to a lower value. Thus, a lower voltage will be generated by the voltage regulator 93 and supplied to the bridge network. Prior to activation of amplifier 151, the voltage regulator 93 supplies a fixed voltage to the bridge network as dictated by resistors 101 and 102 and rheostat 100.

Optionally, the circuit shown in FIG. 3 can include a biasing network extending from the point between the active element 80 and reference element 81 to the output of amplifier 151. As shown, the biasing network includes, in series, a resistor 160 connected to the anode of a zener diode 161, and diode 162 having its cathode connected to the cathode of the zener diode 161 and having its anode connected to the output of amplifier 151. This biasing network insures that the gas sensor is not sent into deep shutoff during excessive temperature conditions and makes sure that the recovery time is kept to a minimum. When the output of amplifier 151 becomes high enough to overcome the drop across the zener diode 161, which comes about during excess temperature conditions on the gas sensor, then a small amount of current will be trickled back into the instrumentation amplifier 106. This small amount of current will keep the sensor from shutting off completely.

Figure 4:
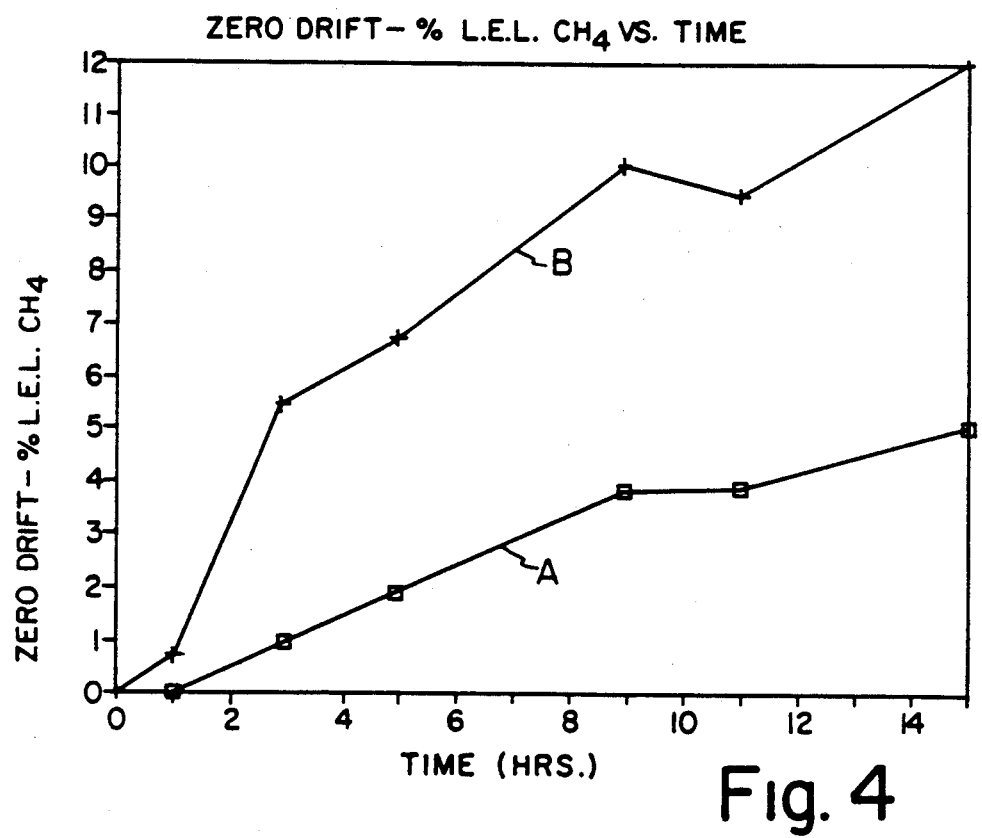
FIG. 4 is a graph showing the improvement in zero drift of the present invention.

A gas sensor system in accordance with the arrangement shown in FIG. 2 was built both with the protection system of the present invention and in a unprotected version. The sensors were exposed to 10% by volume methane for a period of 15 hours, during which checks were made at the zero drift and span drift on 2.5% methane. The graph shown in FIG. 4 is a comparison of the drift generated by the sensors with the protected circuit of the present invention (curve A) as compared with an unprotected circuit (curve B). Span drift of the sensor when connected to the circuit of the present invention showed increases in span of only about 3% of the lower explosive limit as compared to the unprotected circuit which had increases of 10% to 12% of the lower explosive limit. The dramatic difference between curve A and curve B shows the improved zero drift developed as a result of the present invention. In addition, the protected sensor had no reduction in sensor output over time, while the unprotected sensor had a reduction in sensor output of upwards of 50%.

Having described above the presently preferred embodiments of this invention, it is to be understood that it may be otherwise embodied within the scope of the appended claims.

We claim:

1. A temperature limited catalytic gas detector comprising:
    a catalytic gas sensor containing an active element contained in a Wheatstone bridge network;
    a power supply connected through a control means to said bridge network;
    measurement means connected to said bridge network for measuring electrical imbalances across said bridge network which are developed as a particular gas contacts said gas sensor;
    display means connected to said measurement means for displaying the concentration of gas at said gas sensor;
    limit signal means for producing a fixed, predetermined limit signal; and
    comparison means connected to said measurement means and to said limit signal means for comparing an output of said measurement means with the fixed, predetermined limit signal and producing an output signal when the output of said measurement means exceeds said limit signal, and said control means is connected to the comparison means and responsive to the output of said comparison means to thereby reduce the power supplied to said bridge network, and cause said limit signal to be equivalent to the output of said measurement means when said gas sensor is at a particular temperature.

2. The detector of claim 1 wherein said active element is in series with a reference element in one branch of said bridge network.

3. The detector of claim 1 wherein said measurement means is an instrumentation amplifier and said display means is a meter.

4. The detector of claim 1 wherein said control means is a voltage controlled regulator.

5. The detector of claim 1 wherein said comparison means is an on/off comparator.

6. The detector of claim 1 further containing a 4–20 milliampere transmitter connected between the measurement means and display means and connected to said bridge network.

7. The detector of claim 1 wherein said limit signal means is a band gas reference.

8. The detector of claim 1 wherein said limit signal means is a resistive network connected to a fixed voltage source.

9. The detector of claim 1 further containing an alarm means connected to said comparison means for indicating when the temperature at said gas sensor exceeds said particular temperature.

10. The detector of claim 9 wherein said alarm means is a light emitting diode.

11. A temperature limited gas detector apparatus comprising:
    a gas sensor contained in a detection circuit;
    a power supply connected through a control means to said detection circuit;
    means connected to said detection circuit for measuring electrical signals generated by said detection circuit as a particular gas contacts said gas sensor;
    display means connected to said measuring means;
    limit signal means for producing a fixed, predetermined limit signal; and
    comparison means connected to said measurement means and to said limit signal means for comparing an output of said measurement means with the fixed, predetermined limit signal and producing an output signal when the output of said measurement means exceeds said limit signal, and said control means is connected to the comparison means and responsive to the output of said comparison means to thereby reduce the power supplied to said detection circuit, and cause said limit signal to be equivalent to the output of said measuring means when said gas sensor is at a particular temperature.

12. The detector of claim 11 wherein said measuring means is an instrumentation amplifier and said display means is a meter.

13. The detector of claim 11 wherein said control means is a voltage controlled regulator.

14. The detector of claim 11 wherein said comparison means is an on/off comparator.

15. The detector of claim 11 further containing a 4-20 milliampere transmitter connected between the measuring means and display means and connected to said detection circuit.

16. The detector of claim 11 wherein said limit signal means is a band gap reference.

17. The detector of claim 11 wherein said limit signal means is a resistive network connected to a fixed voltage source.

18. The detector of claim 11 further containing an alarm means connected to said comparison means for indicating when the temperature at said gas sensor exceeds said particular temperature.

19. The detector of claim 18 wherein said alarm means is a light emitting diode.

20. A temperature limited catalytic gas detector comprising:

a catalytic gas sensor containing an active element in series with a reference element in one branch of a Wheatstone bridge network;

a power supply connected through a voltage controlled regulator to said bridge network;

an instrumentation amplifier connected to said bridge network for measuring electrical imbalances across said bridge network;

a display connected to said instrumentation amplifier and displaying the concentration of a gas contacting said gas sensor;

limit signal means for producing a fixed, predetermined limit signal; and comparison means connected to said instrumentation amplifier and to said limit signal means for comparing an output of said instrumentation amplifier with the fixed, predetermined limit signal and producing an output signal when the output of said measurement means exceeds said limit signal, and said voltage controlled regulator is connected to the comparison means and responsive to the output of said comparison means to thereby reduce the power supplied to said bridge network, and cause said limit signal to be equivalent to the output of said instrumentation amplifier when said gas sensor is at a particular temperature.

* * * * *

UNITED STATES PATENT AND TRADEMARK OFFICE
CERTIFICATE OF CORRECTION

PATENT NO. : 5,055,269

DATED : October 8, 1991

INVENTOR(S) : Perry A. Palumbo, Oscar Singleton and Louis G. Gaetano

It is certified that error appears in the above-identified patent and that said Letters Patent is hereby corrected as shown below:

Title page, item [54], "DETECTOR" should read --DETECTION--.

Abstract Line 12 "voyage" should read --voltage--.

Column 1 Line 3 "DETECTOR" should read --DETECTION--.

Column 2 Line 10 after "section" insert --,--.

Claim 5 Line 26 Column 10 "1" should read --4--.

Claim 7 Line 33 Column 10 "gas" should read --gap--.

Claim 14 Line 3 Column 11 "11" should read --13--.

Signed and Sealed this

Twentieth Day of April, 1993

*Attest:*

MICHAEL K. KIRK

*Attesting Officer*   Acting Commissioner of Patents and Trademarks